(12) United States Patent  
Cappiello

(10) Patent No.: US 7,959,801 B2
(45) Date of Patent: Jun. 14, 2011

(54) DEVICE FOR GENERATING MICRO- AND NANOFLOW MOBILE PHASE GRADIENTS FOR HIGH-PERFORMANCE LIQUID CHROMATOGRAPHY

(75) Inventor: Achille Cappiello, Urbino (IT)

(73) Assignee: Dani Instruments S.p.A., Cologno Monzese (IT)

( * ) Notice: Subject to any disclaimer, the term of this patent is extended or adjusted under 35 U.S.C. 154(b) by 0 days.

(21) Appl. No.: 12/674,894

(22) PCT Filed: Sep. 8, 2008

(86) PCT No.: PCT/EP2008/061862
§ 371 (c)(1),
(2), (4) Date: Mar. 22, 2010

(87) PCT Pub. No.: WO2009/049967
PCT Pub. Date: Apr. 23, 2009

(65) Prior Publication Data
US 2011/0049031 A1 Mar. 3, 2011

(30) Foreign Application Priority Data
Oct. 16, 2007 (IT) .............................. VE2007A0072

(51) Int. Cl.
B01D 15/08 (2006.01)

(52) U.S. Cl. ..................... 210/198.2; 210/101; 210/143; 210/656

(58) Field of Classification Search .................. 210/635, 210/656, 659, 101, 143, 198.2; 422/70
See application file for complete search history.

(56) References Cited

U.S. PATENT DOCUMENTS
5,011,608 A 4/1991 Damjanovic
7,135,111 B2 * 11/2006 Deguchi et al. ............ 210/198.2
7,141,161 B2 * 11/2006 Ito ............................... 210/198.2
(Continued)

OTHER PUBLICATIONS

Cappiello et al.., Variable-gradient generator for micro- and nano-HPLC, Analytical Chemistry, American Chemical Society, vol. 75, No. 5, Mar. 1, 2003, pp. 1173-1179, at p. 1174, col. 1, lines 13—p. 1177, col. 2, line 16; Figs. 1, 2.
Anonymous, Upchurch nonopeak and microsplitter valves, Chomtech Catalog, Feb. 21, 2007, p. 173, col. 2.

(Continued)

Primary Examiner — Ernest G Therkorn
(74) Attorney, Agent, or Firm — Themis Law

(57) ABSTRACT

A device for generating micro- and nanoflow mobile phase gradients for high performance liquid chromatography includes a generator of micro- and nanoflows of at least two mobile phases in different percentage compositions; an n-position gradient distributor having inlet and outlet ports and n couples of ports for a like number of capillary loops, each selectively connectable at one end with the inlet port and at its other end to the outlet port, which in turn is connectable to an analytical circuit that includes a chromatographic column and a detector; a micro- and nanoflow meter connected to the analytical circuit; a flow deviator having an inlet connected to the outlet of the gradient distributor, one outlet connected to a discharge and another outlet connected to the micro- and nanoflow meter, and a control unit that includes means of control of the generator of micro- and nanoflows such to create the different mobile phase mixture compositions, means for controlling the gradient distributor, means for controlling the position of the flow deviator and means for controlling the throughput of the generator of micro- and nanoflows on the basis of data received from the micro- and nanoflow meter.

10 Claims, 3 Drawing Sheets

U.S. PATENT DOCUMENTS

| | | | |
|---|---|---|---|
| 7,396,469 B2 * | 7/2008 | Andrews et al. | 210/656 |
| 2004/0108273 A1 * | 6/2004 | Richardson et al. | 210/656 |
| 2005/0098487 A1 | 5/2005 | Ito | |
| 2006/0157392 A1 | 7/2006 | Best | |
| 2006/0186028 A1 * | 8/2006 | Hughes | 210/198.2 |
| 2009/0294363 A1 * | 12/2009 | Liu | 210/656 |

OTHER PUBLICATIONS

Anonymous, Equipment News, Analytical Proceedings, vol. 28, Dec. 1991, p. 424, col. 2, lines 3-19.

PCT, International Preliminary Report on Patentability, Sep. 16, 2009.

* cited by examiner

DEVICE FOR GENERATING MICRO- AND NANOFLOW MOBILE PHASE GRADIENTS FOR HIGH-PERFORMANCE LIQUID CHROMATOGRAPHY

REFERENCE TO RELATED APPLICATIONS

This application is a 371 of PCT/EP08/61862 filed Sep. 8, 2008.

FIELD OF THE INVENTION

The present invention relates to a device for generating micro- and nanoflow mobile phase gradients for high-performance liquid chromatography.

BACKGROUND OF THE INVENTION

Recent decades have seen a progressive miniaturization of high-performance liquid chromatography (HPLC) systems, in particular with regard to the mobile phase flows utilized. This is because flow reduction particularly enables the consumption of costly toxic solvents to be limited; it also results in a reduction in injection volumes, and hence enables very small sample quantities to be processed. In addition, if concentration-sensitive sensors are used, a sensitivity increase results because of the smaller dilution of solvent in the column and a better signal-noise ratio.

Finally, the new liquid chromatography-mass spectrometry (LC-MS) coupling techniques enable working at flows less than 1 µL/min, to obtain higher sensitivity and limit possible contamination risks.

However one of the problems encountered when working at very low flows consists of the lack of instrumentation able to generate reliable mobile phase gradients, with only a small delay and homogeneous mixing of solvents. The generation of a gradient at flows less than 1 µL/min certainly requires an adequate pumping system, able not only to carefully and homogeneously mix the mobile phases, but also to transfer them into the column in a reproducible manner and with minimum delay. However, under these conditions the commercially available instrumentation is compelled to operate at its limit, and hence the performance reliability is often questionable. Moreover the effective gradient profile presents an unsatisfactory pattern compared with that set.

One of the most common ways of generating micro- and nanoflow mobile phase gradients is the split-flow technique using a splitter inserted between the HPLC pumps and the injector. This solution is limited by poor control of the gradient actually transferred into the column, and consequently of poor reproducibility. One of the initial attempts to achieve nano-scale gradients was to store a specific gradient in a capillary and to then transfer it into the column with a syringe pump. Drawbacks of this system are poor practicality, a limited choice of gradients to be formed, and poor control of the shape of the gradient.

Another known system, known as the exponential dilution method, consists of rapidly passing the mobile phase flow from the weak eluent, contained in a mixing chamber, to the strong eluent, with generation of a gradient of concave exponential profile.

The drawback of this system is the limited number of gradient types which can be generated.

To overcome this drawback, it has already been proposed to fill the mixing chamber with the weak eluent and to cause the strong eluent to flow in a programmed manner into a dynamic mixer, in order to be able to control the gradient variation with time.

The drawback of this system is a poor versatility of achievable gradient profiles.

Another known system consists of generating an exponential nanoflow gradient by introducing into two successive mixing chambers firstly the weak eluent and then the strong eluent, and then transporting them into the column using one pump at a time.

The drawback of this known solution consists of a limited gradient and profile selection, in addition to a consistent gradient delay.

U.S. Pat. No. 7,135,111 describes a nanoflow gradient elution device. It comprises a first pump for mixing different solvents and transporting them, a second pump for transporting a transfer solution, an injector, a column and a detection system. Two loops enable different solvent mixtures to be temporarily stored, these being transferred by the first microflow pump and then transported into the nanoflow column by the second pump, by a modification in the internal system connections and hence in the flow direction.

The difficulty of this known solution is the difficulty of delivering the mobile phase at constant flow when working with nanolitres/min.

U.S. Pat. No. 7,141,161 describes a gradient pump arrangement able to transfer eluents to a chromatograph continuously, at specific time intervals and at a constant flow of the order of nanolitres/minute while the composition of two or more eluents is modified. The gradient pump arrangement includes a ten-port multi-position valve, a first loop connected to an isocratic pump and a second loop, through which the eluents are transferred.

The drawback of this known solution consists of a considerable complexity of the pump and valve system, making it particularly difficult to automate the instrumentation.

From Cappiello A. et Al "Variable-Gradient Generators for Micro and NanoHPLC", Anal. Chem. 2003, 75, 1173-1179 a device is known for generating micro- and nanoflow mobile phase gradients for liquid chromatography.

SUMMARY OF THE INVENTION

The object of the invention is to improve this known device in order to render it apt to generate micro- and nanoflows automatically, at fast operating speed, with very high flexibility in the choice of the trend of the gradient, in compliance with the analytical needs, and always in very high standards of accuracy and repeatability.

This object is attained with a device for generating micro- and nanoflow mobile phase gradients for high performance liquid chromatography that includes a generator of micro- and nanoflows of at least two mobile phases in different percentage compositions; an n-position gradient distributor having inlet and outlet ports and n couples of ports for a like number of capillary loops, each selectively connectable at one end with the inlet port and at its other end to the outlet port, which in turn is connectable to an analytical circuit that includes a chromatographic column and a detector; a micro- and nanoflow meter connected to the analytical circuit; a flow deviator having an inlet connected to the outlet of the gradient distributor, one outlet connected to a discharge and another outlet connected to the micro- and nanoflow meter, and a control unit that includes means of control of the generator of micro- and nanoflows such to create the different mobile phase mixture compositions, means for controlling the gradient distributor, means for controlling the position of the flow deviator and means for controlling the throughput of the generator of micro- and nanoflows on the basis of data received from the micro- and nanoflow meter.

BRIEF DESCRIPTION OF THE DRAWINGS

Two preferred embodiments of the present invention are further clarified hereinafter with reference to the accompanying drawings, in which.

DETAILED DESCRIPTION OF THE INVENTION

Figure 1:
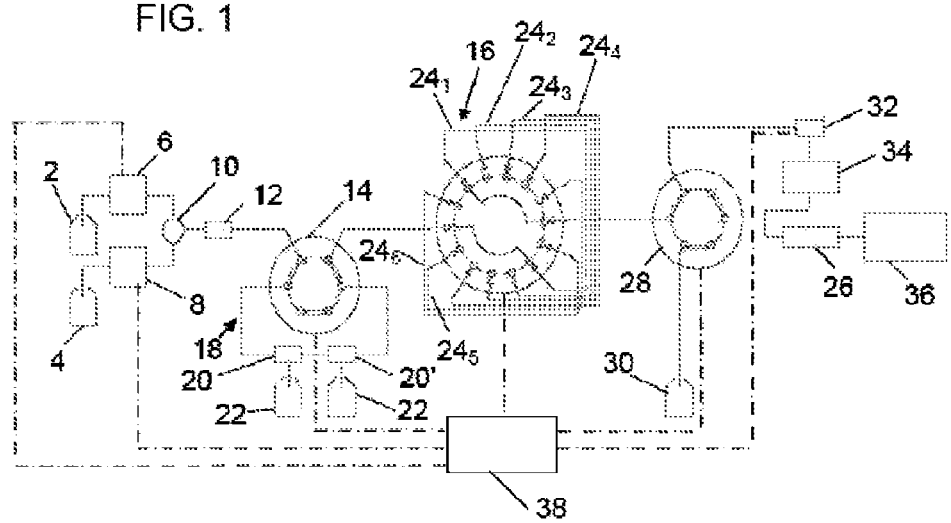
FIG. 1 is a schematic view of a first embodiment of the device of the invention, with two conventional HPLC pumps connected to a splitter device.

With reference to FIG. 1, the first embodiment of the device of the invention is intended for generating micro- and nano-gradients.

It comprises two bottles 2, 4 of two solvents A and B; these are connected via two traditional reciprocating HPLC pumps 6, 8 to a mixer 10 connected to a sintered filter 12 with 0.5 μm pores. This filter is connected to the inlet of a multi-position valve 16 via a splitter circuit indicated overall by 18.

This splitter circuit comprises a valve 14 and two identical PEEKsil capillaries (25 or 50 μm I.D.) connected to the valve via a circuit of small dead volume, and also connected to discharge 22. The splitter circuit 18 enables the desired flow to be obtained from the high flow generated by the HPLC pumps 6, 8 by virtue of the impedance offered by the two capillaries 20, 20' and by the chromatography column 26, fed by the device of the invention.

The multi-position valve 16 is of traditional type, for example model EMTCST6UW of the Valco Instruments Co. Inc., Houston, Tex., and is provided with fourteen ports, two of which form the inlet and outlet, while the other twelve represent the connection points for six loops $24_i$, formed with PEEK tubing of internal diameter 250 μm, to store the mobile phase.

The first five loops $24_1$-$24_5$ are of equal volume of 50 μL, whereas the sixth loop has a volume of 150 μL. It contains the final gradient composition, its greater volume being useful to complete the chromatographic analysis and to clean the column 26.

The outlet port of the multi-position valve 16 is connected to the inlet of a two-position valve 28, having one outlet connected to discharge 30 and the other outlet connected to a micro- and nanoflow meter 32 connected to an injector 34 for the chromatography column 26, with which a detector 36 is associated.

The operation of each device component, and in particular of the two two-position valves 14 and 28 and the multi-position valve 16, is coordinated by a control system 38, providing organized automatic operation of the device.

In operation, the first scheduled operation consists of loading the six loops 24, associated with the multi-position valve 16. To achieve this loading, the two two-position valves 14 and 28 are set with the valve 14 by-passing the splitter device 18 and the valve 28 connecting the outlet of the multi-position valve 16 to discharge 30.

In this configuration the pumps 6 and 8 can provide a high flow, of about 0.8-1.0 mL/min to accelerate the procedure. The control system activates a control program for the pumps 6 and 8, correlated with a program of implementation times for the multi-position valve 16, to distribute the different mobile phase compositions of increasing eluting power within the six loops $24_i$.

For example, to generate a gradient from 100% of solvent A contained in the bottle 2, to 100% of solvent B contained in the bottle 4, the first loop $24_1$ is selected and simultaneously the pump 6 is programmed to alone pump 100% of solvent A; for a flow of 0.8-1.0 mL/min, the time for filling the loop would in theory be just a few seconds, however in practice it is advisable to wait a couple of minutes for conditioning. Thus after a few minutes the loop $24_1$ is completely loaded with its corresponding mobile phase composition, and the control system activates the multi-position valve 16 to connect the second loop $24_2$ to the valve 14; at the same time the operation of the pumps 6 and 8 is modified such that the pump 6 pumps 80% of solvent A and the pump 8 pumps 20% of solvent B.

After another couple of minutes the third loop $24_3$ is selected and the pumps are further modified, such as to pump 60% of solvent A and 40% of solvent B.

The process is then repeated until the sixth loop $24_6$ is selected, with the pump 8 being programmed to alone deliver 100% of solvent B.

Having completed loading of the loops $24_i$, the first loop $24_1$ is again selected, with 100% solvent A passage; the flow is then reduced and the two two-position valves 14 and 28 are switched over to insert the splitter circuit and connect the multi-position valve 16 to the analytical circuit. The system processes the data arriving from the nanoflow meter 32 and regulates the flow of the pump 6 to obtain the desired flow in the column 26.

In this configuration, a micro- or nanoflow of solvent A, originating from the splitter circuit 18, continuously recharges the first loop $24_1$ with the weaker eluent (generally water) to condition the column 26.

Following introduction of the sample and commencement of chromatographic analysis, the multi-position valve 16 is activated to transfer into the column 26 the contents of the next loop $24_2$, loaded with a mobile phase composition of greater eluting power. This process is repeated sequentially for all loops. The pattern of the gradient which is to be generated is obtained by varying the implementation and residence times. The solvent A, which is used without variation to push the contents of each loop until termination of the analysis, enables a constant mobile phase flow to be delivered.

No modification to the conventional chromatograph is required to install the device of the invention. This aspect is particularly important, as it enables any commercially available conventional HPL chromatograph to work effectively with micro- and nanoflows.

Because of the low flow used, the small diameter of the loops $24_i$, and the connection capillaries, no turbulence phenomenon or mixing occurs; consequently once completely filled, the six loops $24_i$ are able to provide eluent sufficient for different analyses, depending on the flow.

The control system stores in its memory the quantities of solvent used by each loop $24_i$ during each analysis, according to the type of gradient and the flow used: this means that before the loops $24_i$ have been completely emptied of the corresponding mobile phase composition, and hence before they are incapable of generate the correct gradient, a new loading procedure is automatically started.

To evaluate the characteristics and performance of the device of the invention, the intraday repeatability was verified by carrying out five analyses of a mixture of four compounds monuron, difenoxuron, linuron and azinphos ethyl, each at a concentration of 5 mg/L.

The separations were obtained with an Agilent Zorbax 150 mm×75 μm column packed with 3.5 μm particles of phase C 18, using a linear gradient from 0% to 100% of $CH_3CN$ in $H_2O$ in 16 min; injection volume 50 nL and detecting with UV at λ=230 nm.

Figure 2:
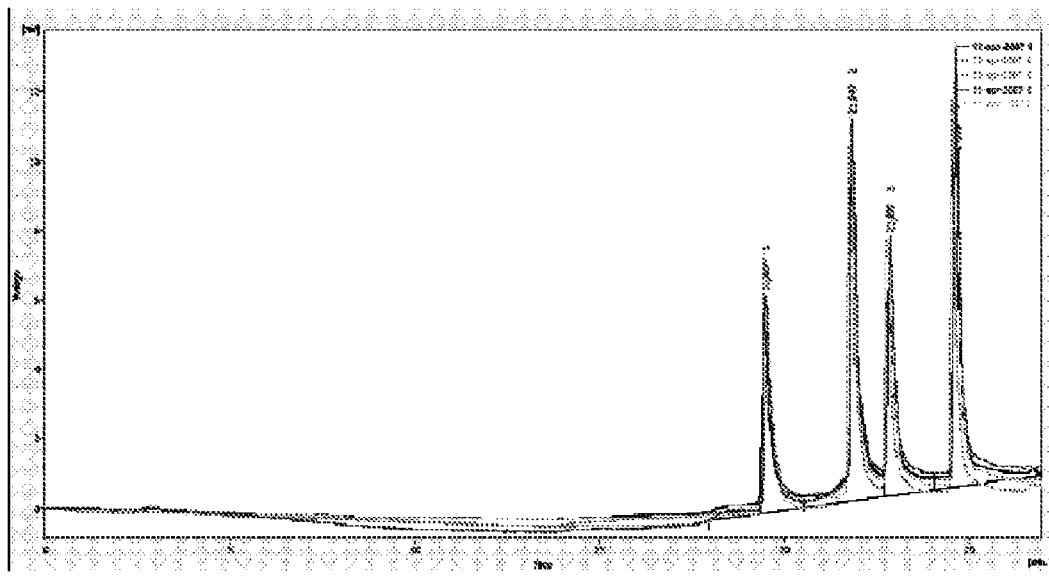
FIG. 2 shows five replicas of the chromatographic separation of a mixture of four components at a predetermined concentration.

FIG. 2 shows the high retention time repeatability in the five analyses, the relative standard deviation being less than 0.19%.

Table 1 shows the retention times relative to the chromatograms of FIG. 2, for a more detailed evaluation of the intraday repeatability.

Figure 3:
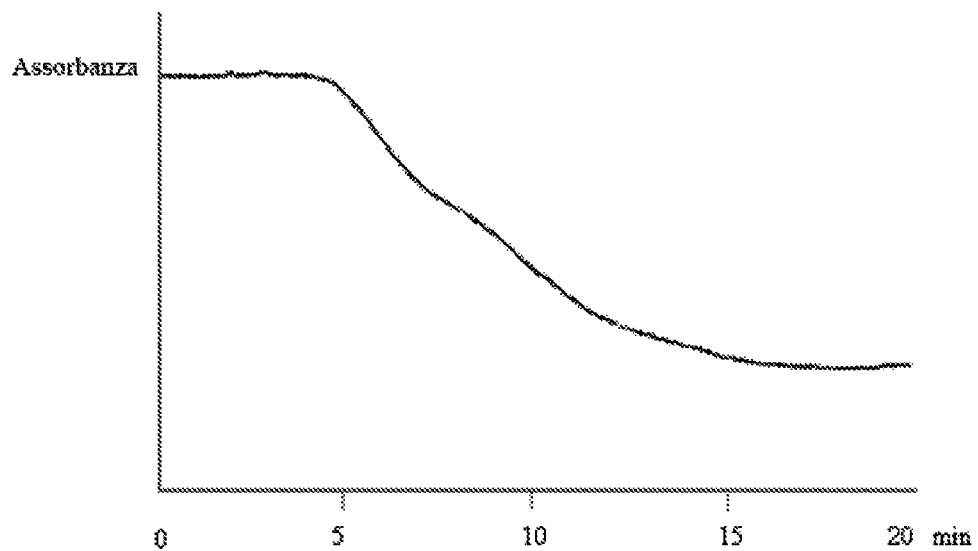
FIG. 3 shows the profile of a stepless trimmed gradient.

FIG. 3 shows a stepless trimmed gradient.

Figure 4:
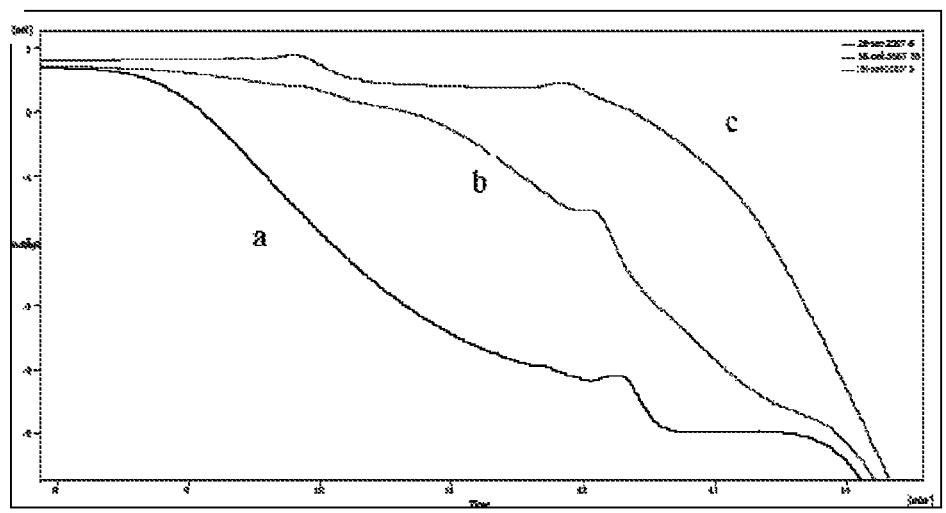
FIG. 4 shows three different profiles of a gradient from 0% to 100% of $CH_3CN$ in $H_2O$ under particular chromatographic conditions.

FIG. 4 shows the profiles of three 12 minute gradients obtained at a flow of 400 nL/min, using different valve operating programs.

The loops $24_i$ were filled with the following solvent compositions: loop $24_1$: 100% $H_2O$-0% $CH_3CN$; loop $24_2$ 80% $H_2O$-20% $CH_3CN$; loop $24_3$: 60% $H_2O$-40% $CH_3CN$; loop $24_4$: 40% $H_2O$-60% $CH_3CN$; loop $24_5$: 20% $H_2O$-80% $CH_3CN$; loop $24_6$: 0% $H_2O$-100% $CH_3CN$.

The operating programs were the following: loop $24_2$ for 0.30 minutes, loop $24_3$ for 1 minute, loop $24_4$ for 1.30 minutes, loop $24_5$ for 9.00 minutes for curve a, which represents the concave gradient; loop $24_2$ for 3 minutes, loop $24_3$ for 3 minutes, loop $24_4$ for 3 minutes, loop $24_5$ for 3 minutes for curve b, which represents the linear gradient; loop $24_2$ for 9.00 minutes, loop $24_3$ for 1.30 minutes, loop $24_4$ for 1 minute, loop $24_5$ for 0.30 minutes for curve c, which represents the convex gradient.

Figure 5:
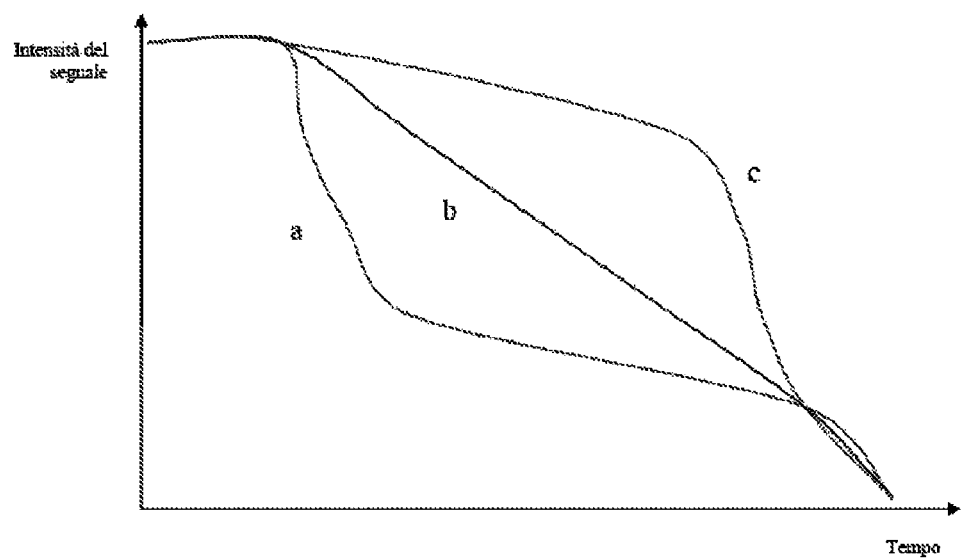
FIG. 5 shows the expected theoretical pattern of the three profiles of FIG. 4.

The expected theoretical patterns are shown in FIG. 5. The traces relative to absorbance are very well differentiated, as shown by the implementation times selected. This is particularly important, considering the extremely small operative flow.

TABLE 1

| Compound | Inj 1 | Inj 2 | Inj 3 | Inj 4 | Inj 5 | $\overline{X}$ | SD | RSD (%) |
|---|---|---|---|---|---|---|---|---|
| Monuron | 19.497 | 19.473 | 19.553 | 19.457 | 19.507 | 19.4974 | 0.03678 | 0.188643 |
| Difenoxuron | 21.847 | 21.780 | 21.833 | 21.847 | 21.830 | 21.8274 | 0.027628 | 0.126574 |
| Linuron | 22.877 | 22.780 | 22.847 | 22.837 | 22.843 | 22.8368 | 0.035302 | 0.154582 |
| Azinphos Ethyl | 24.657 | 24.557 | 24.640 | 24.630 | 24.640 | 24.6248 | 0.039124 | 0.158881 |

In order to also evaluate the interday repeatability, ten chromatographic separations per day were carried out for five consecutive working days. The compounds analysed were: methomyl, monuron, difenoxuron, linuron, each at a concentration of 197 mg/L. The gradient used was from 100% $H_2O$ to 100% $CH_3CN$ in 16 min. Flow 360 nL/min; column Agilent Zorbax C18 3.5 μm, 150 mm×75 μm; injection volume 60 nL; UV detection at λ=230 nm.

The following Table 2 shows the averages of the retention times of each compound for each working day and the standard deviation relative to the daily averages. Excellent interday repeatability can be observed for each compound.

TABLE 2

| Compound | $\overline{X}$ Day 1 | $\overline{X}$ Day 2 | $\overline{X}$ Day 3 | $\overline{X}$ Day 4 | $\overline{X}$ Day 5 | RSD % |
|---|---|---|---|---|---|---|
| Methomyl | 10.59 | 10.55 | 10.68 | 10.81 | 10.44 | 1.31 |
| Monuron | 14.87 | 14.86 | 14.71 | 14.69 | 14.88 | 0.63 |
| Difenoxuron | 17.21 | 17.13 | 16.98 | 16.94 | 17.10 | 0.65 |
| Linuron | 19.15 | 19.04 | 18.89 | 18.91 | 18.99 | 0.55 |

In general it is advisable to use a gradient without steps, in order to obtain a constant variation in the mobile phase composition with time. In this respect, sudden mobile phase variations, typical of a stepped pattern, correspond to rapid polarity changes, which can interfere unexpectedly with the chromatographic separation in terms both of resolution and of reproducibility.

With nanoflows, the different mobile phases contained in continuous loops alternate to mix together within the spaces of the multi-position valve 16 and the connections, to avoid sudden variations in solvent composition.

The high correspondence between the expected and real gradient pattern under different conditions enables the form of the gradient to be set both via a table of implementation times, and by a more intuitive graphical approach. In this respect, the control system makes it possible to display the gradient profile on the computer screen as a function of the implementation times: each change in the set times is immediately reflected as a corresponding change in the displayed profile.

In the same manner, each gradient profile modification, obtained by dragging the graph with the computer pointer, determines a corresponding modification in tabled implementation times. Consequently each gradient form can be easily programmed by establishing the tabled time parameters or the graphic profile.

When a linear gradient is required the command "Linear Gradient" can be used which, based on the selected duration for the gradient, automatically calculates the implementation times and displays the gradient profile.

Figure 6:
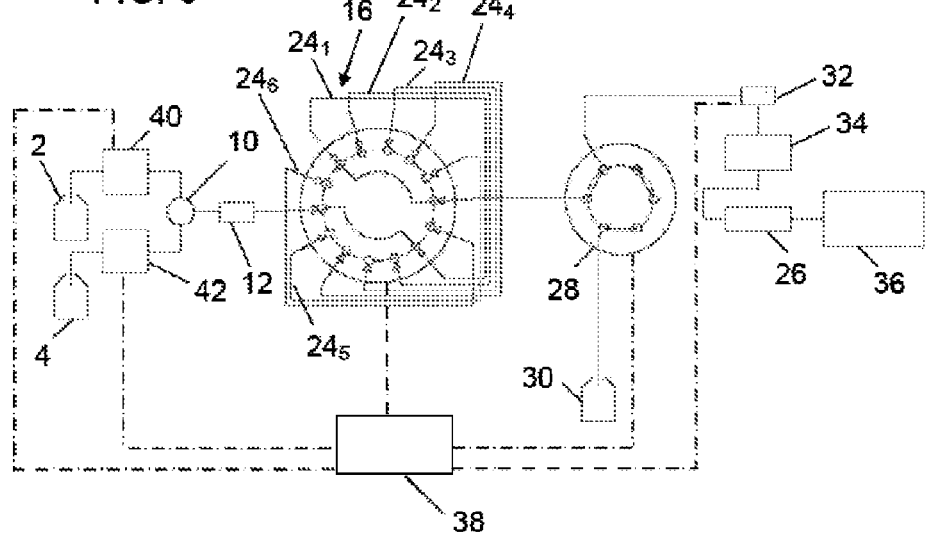
FIG. 6 is a schematic view of a second embodiment of the device of the invention with two HPLC syringe pumps for micro- and nanoflows.

In the embodiment shown in FIG. 6, the device of the invention differs from that shown in FIG. 1 by replacing the reciprocating pumps 6 and 8 by micro- and nanoflow syringe pumps 40 and 42. This enables nanoflows to be obtained without using the splitter circuit 18.

For the rest, the device is similar, with identical components carrying the same reference numerals.

From the foregoing it is apparent that the device of the invention is particularly advantageous, as it enables micro- and nanoflows to be generated automatically, with high flexibility in the choice of the gradient pattern, in accordance with analytical requirements, and always with very high accuracy and reproducibility.

What is claimed is:

1. A device for generating micro- and nanoflow mobile phase gradients for high performance liquid chromatography, comprising:
- a generator of micro- and nanoflows of at least two mobile phases in different percentage compositions;
- an n-position gradient distributor having an inlet port, an outlet port and n couples of ports for a like number of capillary loops, each of the capillary loops being selectively connectable at a first end with the inlet port and at a second end to the outlet port, the second end being connectable to an analytical circuit comprising a chromatographic column and a detector;
- a micro- and nanoflow meter connected to said analytical circuit;
- a flow deviator having its inlet connected to the outlet of said gradient distributor, a first outlet connected to discharge and a second outlet connected to said micro- and nanoflow meter; and
- a control unit comprising,
  - means of control of the generator of micro- and nanoflows such to create the different mobile phase mixture compositions,
  - gradient generating means for controlling said gradient distributor, said gradient generating means acting on implementation and residence time of the different mobile phase mixture compositions,
  - means for controlling a position of said flow deviator, and
  - means for controlling a throughput of said generator of micro- and nanoflows according to information given by said micro- and nanoflow meter.

2. The device as claimed in claim 1, wherein the micro- and nanoflow generator comprises at least two bottles containing different solvents, one or more reciprocating pumps associated with each bottle, a mixer for the flows generated by said pumps, and a splitter circuit.

3. The device as claimed in claim 2, wherein the splitter circuit comprises a valve controlled by said control unit to switch between a position of connection of said bottles to said splitter circuit and a position by-passing said splitter circuit.

4. The device as claimed in claim 3, wherein said splitter circuit comprises at least one capillary connected to said valve and to said discharge.

5. The device as claimed in claim 1, wherein the micro- and nanoflow generator comprises at least two bottles containing different solvents, one or more syringe pumps associated with each bottle, and a mixer for the micro- and nanoflows generated by said syringe pumps.

6. The device as claimed in claim 1, further comprising a filter interposed between said generator of micro- and nanoflows and said gradient distributor.

7. The device as claimed in claim 6, wherein said filter is made of sintered steel with pores of about 0.5 µm.

8. The device as claimed in claim 1, wherein n−1 loops of the gradient distributor have the same volume, and wherein a $n^{th}$ loop has a greater volume.

9. The device as claimed in claim 8, wherein the n−1 loops of the gradient distributor have a volume of about 50 µL, and wherein the $n^{th}$ loop has a volume of about 150 µL.

10. The device as claimed in claim 1, wherein the gradient distributor comprises an n-position valve.

* * * * *